United States Patent [19]
Ortiz et al.

[11] Patent Number: 5,474,549
[45] Date of Patent: Dec. 12, 1995

[54] METHOD AND SYSTEM FOR SCANNING A LASER BEAM FOR CONTROLLED DISTRIBUTION OF LASER DOSAGE

[75] Inventors: Mark V. Ortiz, San Jose; Dirk J. Kuizenga, Sunnyvale, both of Calif.

[73] Assignee: Laserscope, San Jose, Calif.

[21] Appl. No.: 20,255

[22] Filed: Feb. 18, 1993

Related U.S. Application Data

[63] Continuation of Ser. No. 727,559, Jul. 9, 1991, abandoned.

[51] Int. Cl.⁶ ............................................. A61B 17/36
[52] U.S. Cl. .................. 606/9; 606/11; 606/13; 606/17
[58] Field of Search ................... 606/2, 3, 9–18

[56] References Cited

U.S. PATENT DOCUMENTS

| | | | |
|---|---|---|---|
| 4,215,694 | 8/1980 | Isakov et al. | 606/11 |
| 4,665,913 | 5/1987 | L'Esperance, Jr. | 606/11 X |
| 4,718,416 | 1/1988 | Nanaumi | 606/9 |
| 5,035,693 | 7/1991 | Kratzer | 606/12 |
| 5,053,006 | 10/1991 | Watson | 606/2 X |

FOREIGN PATENT DOCUMENTS

WO87/06478  11/1987  WIPO .................... 606/10

*Primary Examiner*—Stephen C. Pellegrino
*Assistant Examiner*—Michael Peffley
*Attorney, Agent, or Firm*—Haynes & Davis

[57] ABSTRACT

A system and method for distributing an output beam from a laser system on a body which provides for a uniform fluence level throughout an entire treatment region. A first structure receives the laser beam and aims it along a propagation axis. A scanner scans the propagation axis of the laser beam at a controlled scan velocity, so that the laser beam essentially continuously scans a treatment pattern on the body. The treatment pattern can consist of an essentially straight line, or a ring, or other pattern which can be easily fitted together with other patterns to fill in a treatment area.

The method includes the steps of:
  supplying a laser beam,
  directing a laser beam along a propagation axis to the body, and
  scanning the propagation axis of the laser beam at a controlled scanned velocity, so that the laser beam essentially continuously scans the treatment pattern on the body.

33 Claims, 5 Drawing Sheets

METHOD AND SYSTEM FOR SCANNING A LASER BEAM FOR CONTROLLED DISTRIBUTION OF LASER DOSAGE

This application is a continuation of Ser. No. 07/727,559, filed Jul. 9, 1991, now abandoned.

FIELD OF THE INVENTION

The present invention relates to an instrument for distributing laser dosage in a treatment pattern, such as used in dermatology for the treatment of angiomas and the like.

DESCRIPTION OF RELATED ART

A condition known as the planar angioma occurs due to hypervasculation of the skin. This hypervasculation causes the skin to appear discolored. This discoloration is commonly known as a "port wine stain".

Current treatments for the planar angioma comprise closing off the blood vessels in the affected zone. This stops blood flow and the resultant discoloration in the hypervascularized area.

The techniques used for closing off the blood vessels involve application of laser beams to the treatment zone. This effects closing off the blood vessels by photocoagulation, when the laser beam is generated at preferred wavelengths, as commonly known in the art.

The photocoagulation occurs due to thermal effects of the impact of the laser beam. In treating angiomas, the thermal effects desired occur in a specific temperature range. This elevated temperature range must be limited to the microvessels in the dermis in order to avoid any tissue damage and scar formation as a result of the procedure.

This laser treatment can be applied manually by a practitioner, or by means of an instrument such as disclosed in International Publication No. WO 87/06478 of International Patent Application No. PCT/FR87/00139, entitled SYSTEMATIZED TREATMENT INSTRUMENT, USING PARTICULARLY LASER ENERGY, USEFUL FOR EXAMPLE IN DERMATOLOGY.

The problems with the manual treatment are explained in the International Publication No. WO 87/06478, and include problems with regulating the distribution of the dosage of radiation and the like in a manner which avoids overexposing certain areas and underexposing other areas. Thus, the skill of the practitioner in applying the treatment is of utmost importance for the manually administered technique.

The International Publication No. WO 87/06478 provides a mechanized instrument for distributing the laser energy. This mechanized instrument involves delivering the laser beam in an optical fiber to a treatment head. In the treatment head, the end of the optical fiber is positioned to expose elementary spots using stepper motors in a sequential scan pattern. A shutter in the treatment head is used to control the duration of pulses at each position in the scan pattern. While this technique has proved to provide great advances over the manual technique, it still suffers certain problems.

In particular, in this prior art system, the dosages of laser radiation are delivered to the treatment area in discreet elementary spots. One spot is irradiated, and then a shutter is closed and the beam delivery apparatus repositioned to a second spot. Then the second spot is illuminated and so on until the entire treatment area is scanned. The shape of the spot is basically circular. Because of the circular shape, it is difficult to position successive elementary spots across the treatment area in a way that provides for a uniform distribution of dosage across the treatment area. Some areas get greater amounts of radiation while others get lesser amounts. This effect can be understood by considering positioning three pennies adjacent to one another. Unless the pennies overlap one another, there must be an open region between the pennies. There are similar open regions which will receive no direct radiation between the spots of the prior art treatment system. This inability to provide a uniform dosage across the entire treatment area has resulted in stipple patterns in the planar angioma regions being treated. To remove the stipple pattern, the angioma must be re-treated to compensate for the underexposed portions. Obviously, re-treatment is costly, and subjects the patient to an increased risk of scarring or other problems that may occur during the procedure.

Furthermore, the very high repetition rates in which the shutter must be opened and closed to illuminate each spot, has resulted in high failure rates in the shutter mechanism. It is difficult to provide a shutter which is durable enough and operates quickly enough, in the portable treatment head which is utilized with such systems.

Accordingly, it is desirable to provide a system and method for treating planar angiomas, and other medical conditions, with a controlled distribution of laser radiation which is more uniform, reliable, and easier to apply than the prior art.

SUMMARY OF THE INVENTION

The present invention provides an apparatus and method for distributing an output beam from a laser system on a body which provides for a uniform fluence level throughout an entire treatment region. Furthermore, it eliminates the need for very high repetition rates of the shutter in the treatment head. Accordingly, the present invention provides a safer and more reliable system for distributing a laser beam across a treatment area in medical applications.

In one aspect, the present invention provides an apparatus for distributing an output beam from a laser. The apparatus includes the first structure which receives the laser beam and directs it along a propagation axis. This structure directing the laser beam is then coupled with a scanner, that scans the propagation axis of the laser beam at a controlled scan velocity, so that the laser beam essentially continuously scans a treatment pattern on the body. Thus, the laser beam is moved across a treatment pattern on the body, rather than held stationary to illuminate an elementary spot as suggested in the prior art.

The treatment pattern can consist of an essentially straight line, or a ring, or other pattern which can be easily fitted together with other patterns to fill in a treatment area. Alternatively, the treatment pattern can be a spiral or raster scan pattern which completely fills a treatment area.

The structure which directs the laser beam in one aspect of the invention includes an optically transmissive fiber which supplies the laser beam, and means for securing the fiber so that the laser beam propagates along a propagation axis transverse to and having a position in a scanning plane. The scanner controls the position of the propagation axis in the scanning plane in order to scan the treatment region. Other mechanisms, such as galvanometer mounted mirrors and the like, may be used for scanning the laser beam.

According to another aspect of the present invention, a method for distributing an output beam from a laser is provided. The method includes the steps of:

supplying a laser beam, directing a laser beam along a propagation axis to the body, and scanning the propagation axis of the laser beam at a controlled scanned velocity, so that the laser beam essentially continuously scans the treatment pattern on the body.

The step of scanning, according to one aspect of the invention, is successively repeated so that the laser beam scans a plurality of essentially continuously scanned treatment patterns, wherein the successive treatment patterns fill a treatment region on the body. The successive treatment patterns can be positioned so that a first sequential treatment pattern is non-adjacent to a next sequential treatment pattern.

According to yet another aspect, the method includes providing a template having an opening defining an outside dimension of the treatment region. With the template, the step of scanning includes turning on the laser beam while the propagation axis directs the laser beam outside of the opening of the template. Next, the propagation axis is scanned at a constant velocity across the opening while the laser beam is on until the laser beam is directed outside the opening. While the laser beam is directed outside the opening, the propagation axis is repositioned, with laser beam either on or off, for a successive treatment pattern.

As can be seen, the system and method according to the present invention allows for completely filling a treatment region with a constant fluence level. This minimizes the possibility of stipple patterns and the like being left after a first treatment. Further, the present system includes much lower repetition rates on the shutter mechanism in the treatment head, which improves the reliability of the treatment system.

Other aspects and advantages of the present invention can be seen on review of the figures, the detailed description and the claims which follow.

DETAILED DESCRIPTION

Figure 1:
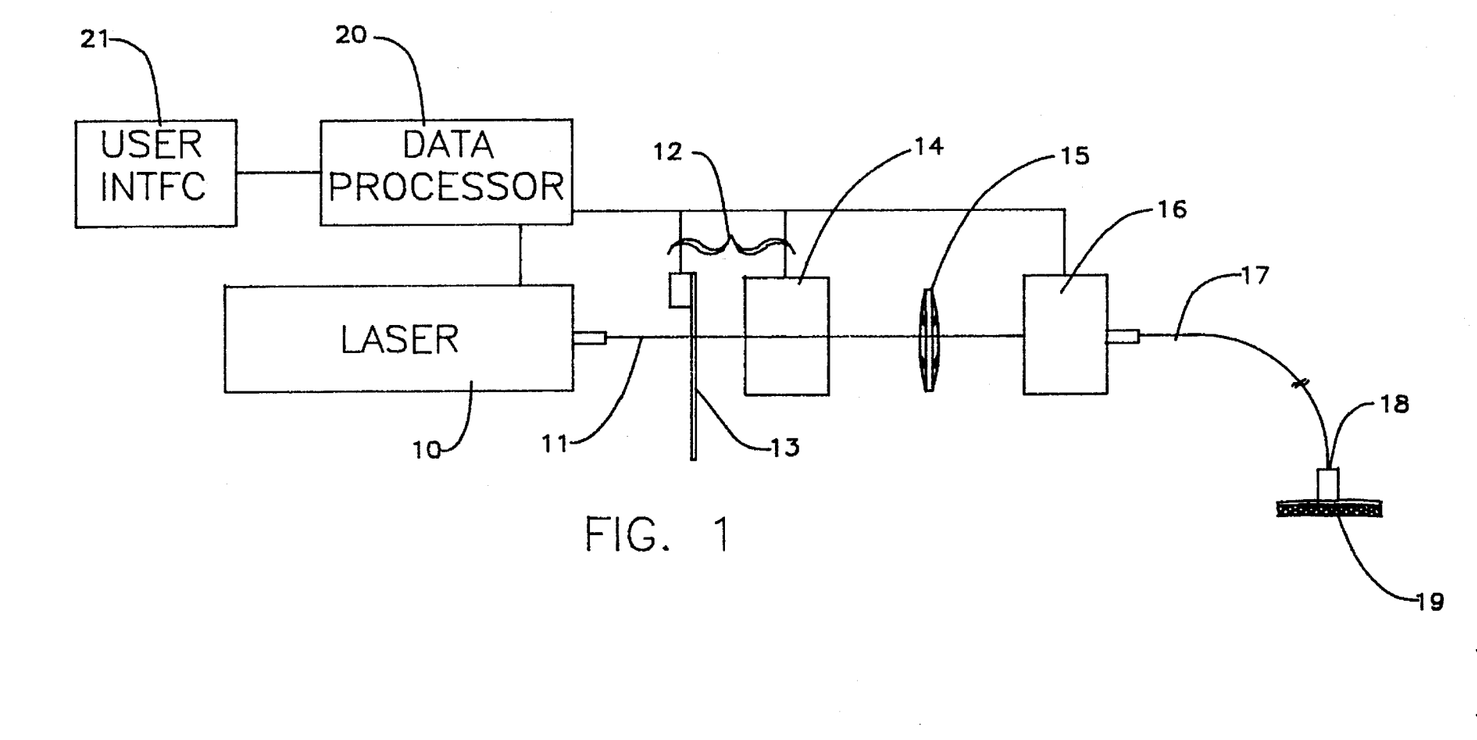
FIG. 1 is a schematic diagram of a laser system for distributing an output beam on a body according to the present invention.
Figure 2:
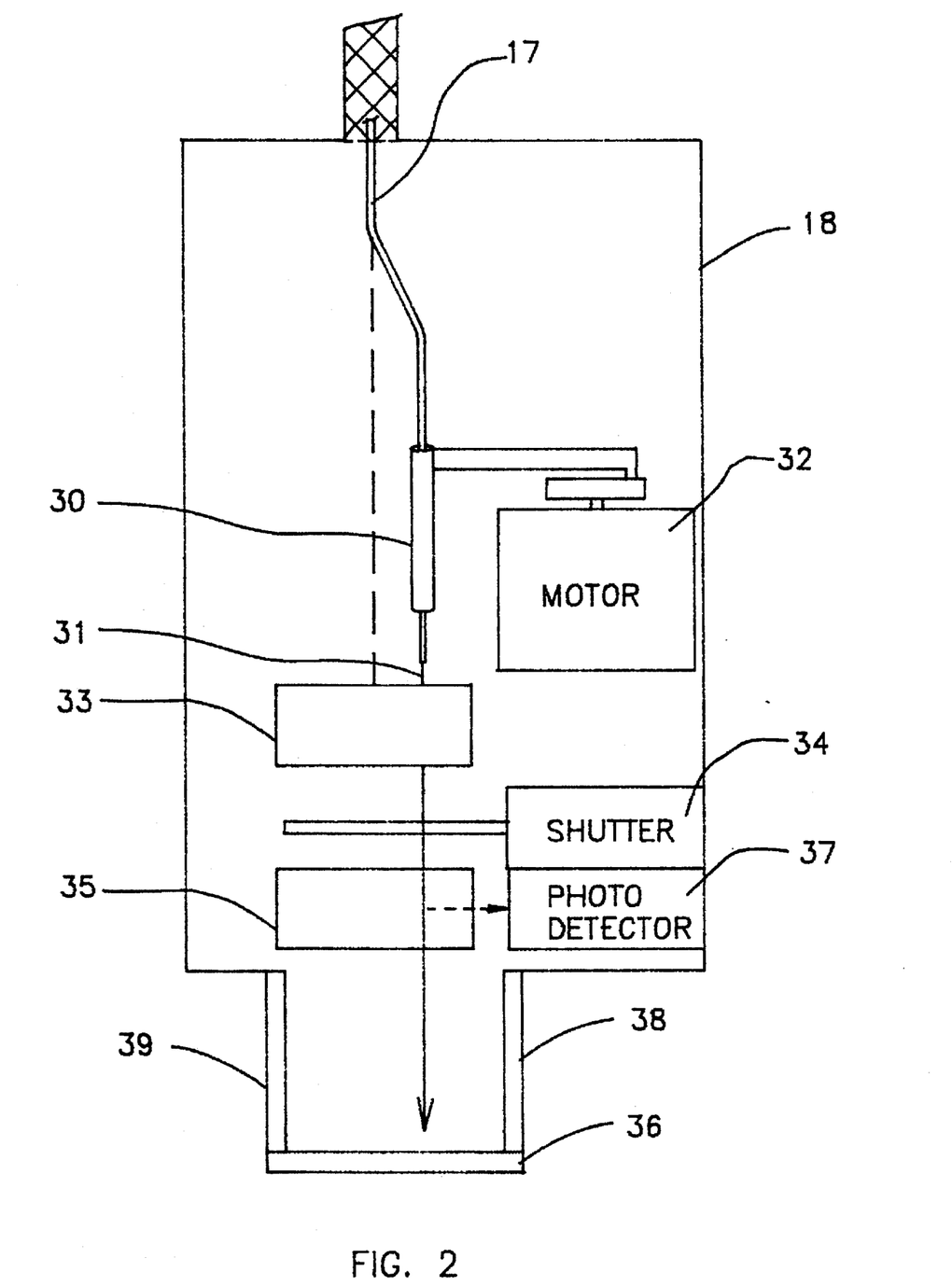
FIG. 2 is a schematic diagram of a treatment head utilizing the laser system of FIG. 1.
Figure 3:
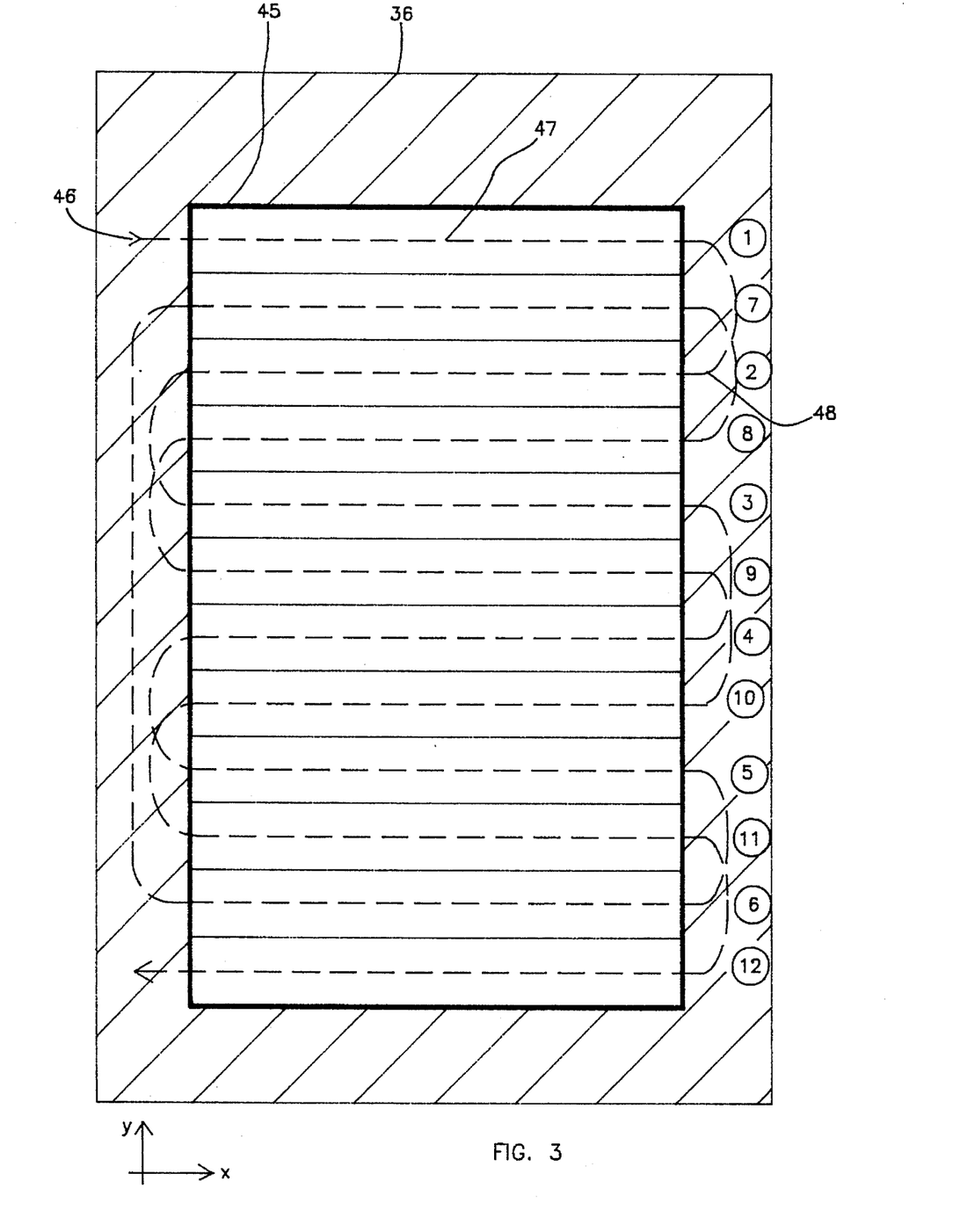
FIG. 3 is a schematic diagram of the template and a plurality of treatment patterns used in conjunction with the system of FIG. 1.
Figure 4:
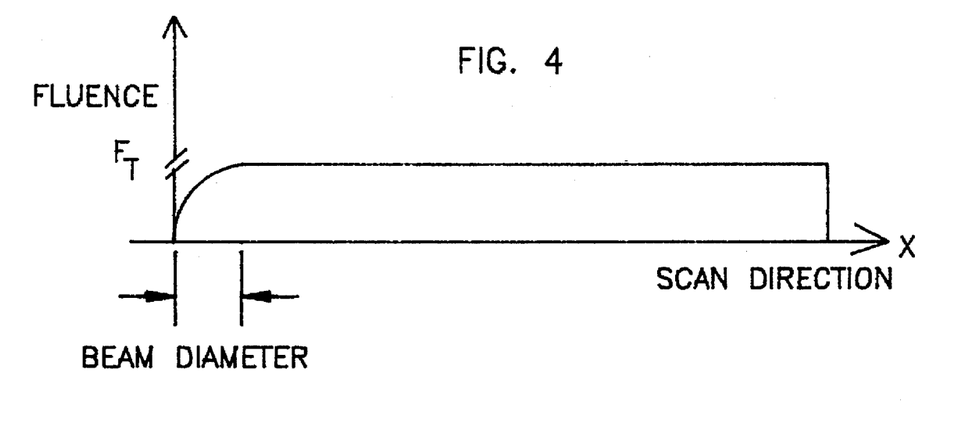
FIG. 4 is a graph showing the fluence versus scan direction for the treatment pattern of FIG. 3.
Figure 5:
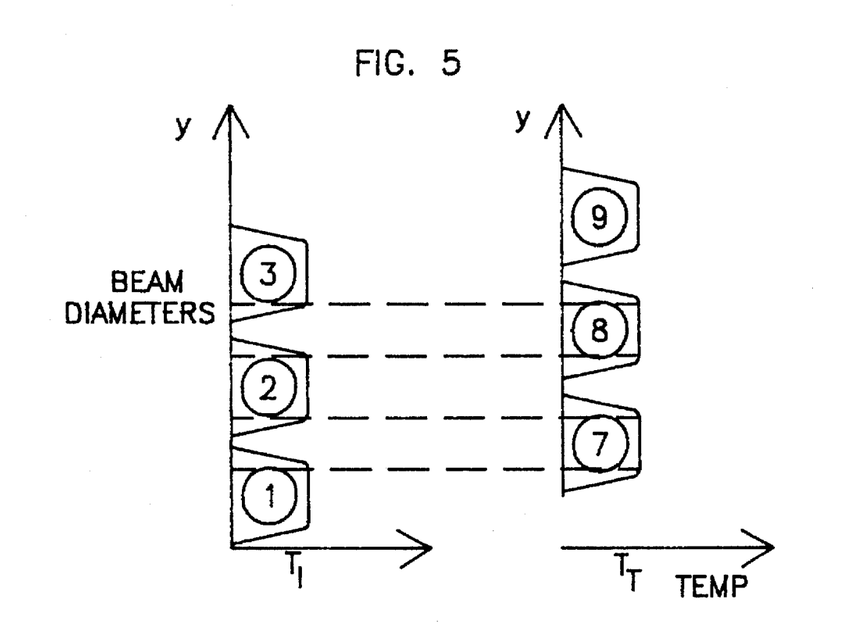
FIG. 5 is a graph showing the temperature profile orthogonal to the scan direction for the treatment patterns in FIG. 3.
Figure 6:
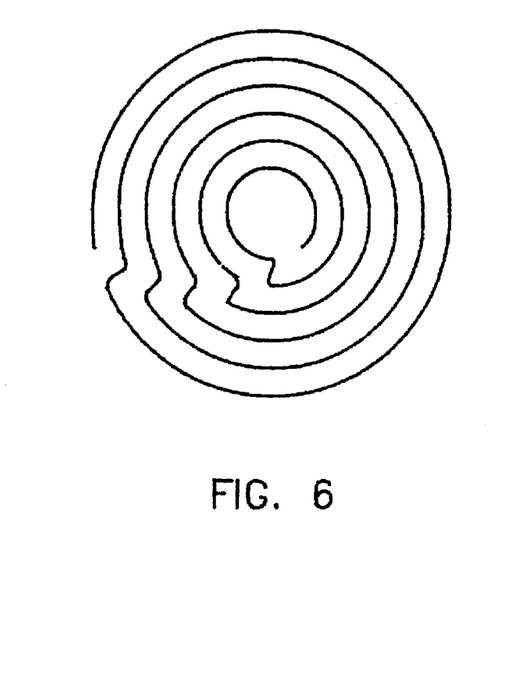
FIG. 6 illustrates an alternative treatment pattern.
Figure 7:
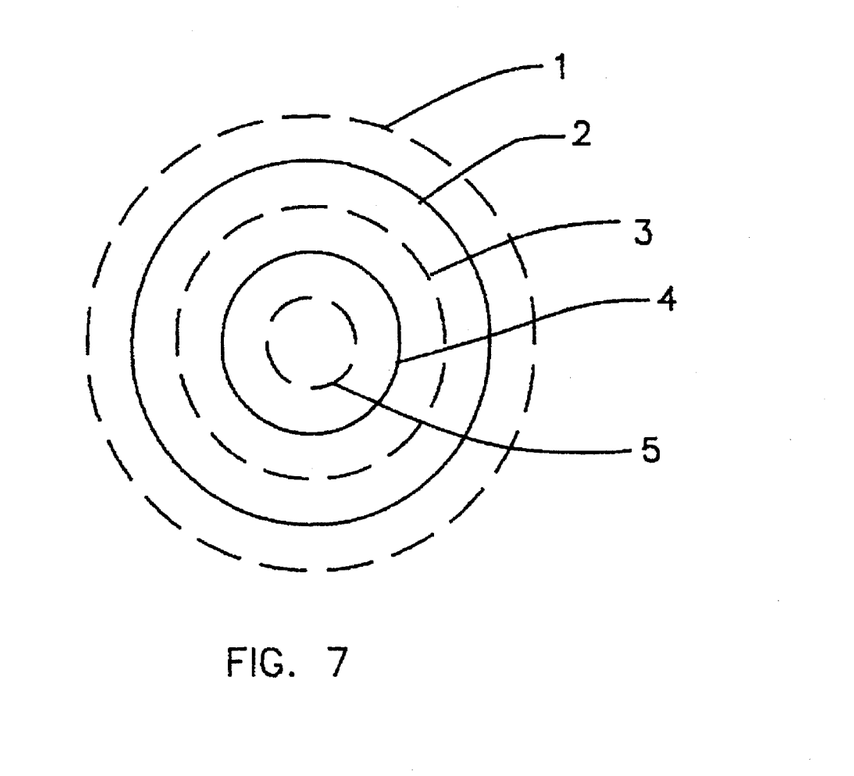
FIG. 7 illustrates another alternative treatment pattern.

A detailed description of an embodiment of the present invention is provided with reference to the figures. FIG. 1 illustrates the system for delivering the laser output beam. FIG. 2 illustrates one construction for the treatment head for distributing the beam. FIGS. 3, 4, and 5 illustrate the operation of the beam distribution technique. FIGS. 6 and 7 illustrate alternative treatment patterns which can be used according to the present invention.

As shown in FIG. 1, the laser system according to the present invention includes a laser 10 which generates an output beam along path 11. The output beam is supplied through external beam path components 12 such as a shutter 13 and an attenuator 14. From the external beam path components 12, the beam is delivered through a lens 15 into a fiber-optic coupler 16. The beam is then delivered through an optical fiber 17 to a treatment head 18, which distributes the laser beam output on a body 19. A data processor 20 is coupled with the laser 10, the external beam path components 12, and the treatment head 18 for controlling operation of the system. User interface 21 is coupled to the data processor 20, for providing user input utilized in controlling the system during treatment.

Intense light sources other than lasers, such as arc lamps, LEDs, etc., can be used as well according to the present invention.

FIG. 2 provides a schematic illustration of a treatment head 18 which can be used in the present invention. This treatment head is similar to that described and disclosed in the above-referenced International Publication No. WO 87/06478. As can be seen, the fiber 17 enters the treatment head 18 and is supplied to an aiming bracket 30. The aiming bracket 30 establishes a propagation axis along which the laser output 31 from the fiber 17 proceeds. This aiming bracket 30 is mounted on a mechanism, such as a plurality of stepper motors (of which motor 32 is representative), which are operative to scan the propagation axis defined by the bracket 30 through a scan plane transverse to the propagation axis. In the preferred system, this plane will be orthogonal to the propagation axis by the bracket 30.

The output 31 from the fiber 17 is supplied through a lens 33 past shutter 34, beam splitter 35, and through a template 36 to the treatment area. A photo detector 37 is coupled with the beam splitter 35 for indicating the intensity of the output light.

The template 36 is mounted on stand-off posts 38, 39 which place the template 36 adjacent to the focal plane of the lens 33.

The lens 33 can be an adjustable lens by which the spot size of the laser beam at the template 36 can be adjusted.

Alternative systems for scanning the propagation axis of the laser beam could include galvanometer-mounted mirrors and the like and a wide range of other equivalent mechanisms known in the art.

FIG. 3 illustrates one embodiment of the template 36 according to the present invention, and a plurality of treatment patterns numbered sequentially 1 through 12.

As can be seen, the template 36 has a rectangular opening 45 which allows passage of a laser beam into a treatment area. The treatment area has been for this example divided into twelve lines, where each line is a treatment pattern to be scanned by the laser beam.

In operation, the laser beam is positioned at point 46 on the template body 36 to begin a treatment. A first treatment pattern is exposed by scanning the laser beam at essentially constant velocity along line 47 across the opening in the template 36 until the laser beam falls outside the opening. Next, the laser beam is positioned for a second treatment pattern at point 48. From point 48 the beam is scanned at an essentially constant velocity across the opening until the propagation axis directs the beam outside the opening 45. These line-shaped treatment patterns are successively scanned in the order illustrated, where each sequential treatment pattern is non-adjacent to the next treatment pattern in the sequence. Thus, as can be seen, treatment patterns 1, 2, 3, 4, 5, and 6 are spaced apart from one another. Treatment pattern 7 is between patterns 1 and 2. Treatment pattern 8 is between patterns 2 and 3. Treatment pattern 9 is between patterns 3 and 4. Treatment pattern 10 is between pattern 4 and 5. Treatment pattern 11 is between patterns 5 and 6. Finally, treatment pattern 12 is between the pattern 6 and the edge of the template 36.

By controlling the intensity of the laser beam and the velocity of scanning of the beam across the treatment patterns, the fluence level throughout the entire treatment area can be precisely controlled, and a uniform distribution of laser energy can be produced. The laser beam can be left on while it is irradiating the template area during repositioning, or it can be turned off using the shutter 34, or the shutter 13 in the external beam path 12. Also, the beam can be turned off using a Q-switch within the laser system itself 10, or other apparatus known in the art. Further, the effect of the template can be achieved by proper timing of the shutter.

The precise control of the fluence level is illustrated with reference to FIGS. 4 and 5. FIG. 4 is a graph of the temperature (trace 100) and fluence (trace 101) level versus scan direction for a particular treatment pattern, e.g. pattern 1, which correlates with the coordinate axes illustrated in FIG. 3. As can be seen, the fluence for a beam which is scanned at an essentially constant velocity with constant intensity across the treatment pattern begins centered at approximately −1 beam diameters at the beginning of the treatment pattern, rises to a constant level $F_T$ approximately one half beam diameter before getting into the treatment pattern, and continues at the constant value $F_T$ until approximately one half beam diameter after the end of the treatment pattern. This insures a constant fluence level. At the end of the treatment pattern on the edge of the template, the transmitted fluence level drops to 0. The treatment temperature $T_T$ induced by this constant fluence level rises rapidly after the edge 102 of the template to the preferred level and remains constant to the opposite edge 103 of the template.

As can be seen, a scan of an essentially constant velocity allows for very even distribution of fluence through a treatment pattern. So long as all of the changes in velocity of the scan, such as occur at turns or when the scan is stopped, occur outside the treatment area on the template or after the shutter is closed, the fluence level in a treatment pattern can be very precisely, and evenly distributed.

For temperature sensitive treatments, such as the treatment of planar angiomas, is desirable to insure that the temperature reached by the entire treatment area is essentially constant, and does not exceed levels which would cause scarring or other damage to the tissue. Therefore, the treatment patterns used to fill the treatment area, are scanned in a manner so that each successive treatment pattern is not adjacent to a next treatment pattern. The thermal effect of this spacing of treatment patterns is illustrated in FIG. 5, where a cross-section of the temperature caused by successive scans is illustrated heuristically. The graph of FIG. 5 includes a first temperature axis which shows the temperature profiles of the scans 1, 2, 3 and so on, and a second temperature axis which shows the temperature profiles of the scans 7, 8, and 9. It can be seen that for scan number 1, the temperature begins at a constant value and rises to the temperature of treatment $T_T$ very quickly within the width of the treatment pattern. At the edge of the treatment pattern, it falls off back to the body temperature. The next treatment pattern, number 2, causes an elevated temperature which does not overlap with the elevation in temperature caused by treatment pattern number 1. A similar effect occurs with treatment pattern number 3. As can be seen, elevated temperature is reached in areas outside the directly exposed scan pattern, due to heat conduction and scattering of the beam.

However, treatment pattern number 7 on the second pass through the treatment area, fills the area which was left untreated between treatment pattern numbers 1 and 2. A similar effect occurs with patterns 8 and 9 and so on.

These patterns 7, 8, and 9 are scanned after the temperature in the edges of the regions reached during the previous scans 1, 2, 3, has relaxed substantially. This effect allows the entire treatment area to be brought to the preferred treatment temperature $T_T$, and insures that no area reaches a temperature which is too high due to elevated temperature generated in a previous treatment pattern.

Because the treatment patterns illustrated in FIG. 3 are essentially straight lines having a finite width, they can be easily fitted together in a way which avoids leaving areas underexposed or overexposed.

The treatment pattern illustrated with respect to FIG. 3 provides that the scan direction for each treatment pattern will alternate, such that treatment pattern number 1 is scanned from left to right, while treatment pattern number 2 is scanned from right to left and so on. If the effects of the reduced temperatures at the beginning of a treatment pattern are critical, the treatment patterns can all be scanned in the same direction, so that the boundary of the uniform fluence level is more continuous.

The template 36 illustrated with respect to FIGS. 3 and 4 is rectangular in shape. However, these templates can be designed in a variety of shapes to meet the needs of a particular laser treatment. Furthermore, the intensity of the laser beam, the rate of scanning and the positioning of the various treatment patterns within the template can be precisely controlled with the data processing system.

Thus, one method of the present invention for distributing a constant fluence level of laser radiation in a treatment includes:

(1) providing a template having an opening defining an outside dimension of a treatment region;

(2) directing a laser beam along a propagation axis through the template; and (3) scanning the propagation axis of the laser beam at a controlled scan velocity so that the laser beam essentially continuously scans a treatment pattern within the template.

The treatment pattern can either completely fill the template, or the step of scanning can be successively repeated so that the laser beam scans a plurality of essentially continuously scanned treatment patterns to fill the treatment region. The distribution of temperature caused by the laser scanning can be controlled further by positioning successively scanned treatment patterns so that a first sequential treatment pattern is positioned non-adjacent to a next sequential treatment pattern.

The step of scanning can be computer controlled so that it includes turning on the laser beam while the propagation axis directs the laser beam outside of the opening of the template, scanning the propagation axis at a constant velocity across the opening while the laser beam is on until the laser beam is directed outside of the opening, and while the laser beam is directed outside of the opening, repositioning the propagation axis of the laser beam for a successive treatment pattern.

Another method of the present invention for distributing a constant fluence level include:

(1) directing a laser beam aiming device to direct a laser beam along a propagation axis toward a treatment region;

(2) beginning to scan the propagation axis and then enabling the laser beam by opening a shutter or other technique, at a controlled position in the treatment region while the propagation axis is being scanned; and (3) continuously scanning the propagation axis of the laser beam at a controlled scan velocity so that the laser beam essentially continuously scans a treatment pattern within the treatment region, and then closing the shutter or disabling the laser beam while the propagation axis is being scanned.

This process can be successively repeated until the laser beam scans a plurality of essentially continuously scanned treatment patterns to fill the treatment region. The treatment pattern will have a width of at least one beam diameter, and a length of more than one, and preferably many, beam diameters. Further, the treatment patterns used to fill a treatment region can take a variety of shapes as suits the needs of a particular situation.

According to this technique, the need for a template is minimized, and the shape of the outside dimensions of the treatment region can be precisely controlled using a computer. It is desirable to have the propagation axis being scanned when the laser beam is enabled so that the beam does not overexpose or underexpose the starting point of the scan.

FIGS. 6 and 7 illustrate alternative treatment patterns which can be utilized according to the present invention.

In FIG. 6, the treatment pattern is essentially a spiral. By shutter control or Q-switch control of the laser light the spiral provides for placing sequential scans 1–5 of the beam non-adjacent previous scans. The spiral can be effectively used to provide a constant fluence level within a treatment area.

FIG. 7 illustrates a treatment pattern consisting of concentric rings having respective radii and radial width. The concentric rings could be scanned such that rings 1, 3 and 5 are scanned in a first pass, and rings 2 and 4 are scanned in a second pass to insure that sequential treatment patterns are non-adjacent.

This computer controlled scanning technique for treatment of dermatology-related disorders with a consistent fluence level throughout the treatment area provides significant advantages over the prior art. It allows for the shape of the treatment area to be precisely controlled, while insuring a constant fluence level which entirely fills the treatment area. With computer control, the intensity and scan velocity can be precisely controlled so that the fluence level actually distributed throughout the treatment area can be selected over a wide range with high accuracy and uniformly distributed.

The preferred laser 10 for dermatological applications such as the treatment of planar angiomas is a Nd:YAG laser providing a frequency-doubled output of 532 nanometers or 659 nanometers, such as is commercially available from Laserscope Corp. in San Jose, Calif. Also, other laser systems such as argon ion lasers, dye lasers, or copper vapor lasers commonly used in dermatology applications can be utilized.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. An apparatus for distributing an output beam from an intense light source on a body for non-invasive treatment, comprising:

a flexible waveguide having a proximal end and a distal end, and coupled to the intense light source on the proximal end;

a portable treatment head for positioning adjacent a treatment area on the body including a housing having a light transmissive opening, and means, coupled to the distal end of the flexible waveguide, for receiving light communicated by the waveguide;

means, mounted with the housing of the treatment head, for directing the light received from the flexible waveguide as an output beam through the transmissive opening to the treatment area;

means, mounted with the housing of the treatment head and coupled with the means for directing, for scanning the output beam in a controlled velocity and direction to define an essentially continuous treatment pattern in the treatment area on the body.

2. The apparatus of claim 1, wherein the treatment pattern consists essentially of a straight line having a width and a length greater than the width.

3. The apparatus of claim 1, wherein the treatment pattern consists essentially of a ring, having a radius and a radial width.

4. The apparatus of claim 1, wherein: the means for directing comprises means for securing the flexible waveguide, so that the output beam propagates along a propagation axis essentially transverse to, and having a position in, a scanning plane; and the means for scanning comprises means, coupled to the means for securing, for controlling the position of the propagation axis in the scanning plane.

5. The apparatus of claim 1, wherein:

the means for scanning comprises means, receiving the output beam from the flexible Waveguide, for controlling position of the beam in the treatment area.

6. The apparatus of claim 1, further including a template mounted on the treatment head to define a perimeter of the transmissive opening.

7. The apparatus of claim 1, further including a structural spacer member, mounted on the treatment head, for establishing a preset distance from a body contacting the treatment head and the means for directing.

8. The apparatus of claim 7, further including a template mounted on the spacer member to define a perimeter of the transmissive opening.

9. A method for distributing an output beam from an intense light source on a body, comprising:

placing portable beam aiming equipment adjacent a treatment area on the body;

supplying the output beam to the beam aiming equipment;

directing the beam aiming equipment to define a propagation axis of the output beam to the body; and scanning the propagation axis of the output beam at a controlled scan velocity, so that the output beam essentially continuously scans a treatment pattern on the body.

10. The method of claim 9, further including:

successively repeating the step of scanning without repositioning the beam aiming equipment so that the output beam scans a plurality of essentially continuously scanned treatment patterns, and wherein the successive treatment patterns fill a treatment region on the body.

11. The method of claim 10, wherein the step of successively repeating includes positioning the successively scanned treatment patterns so that a first sequential treatment pattern is positioned non-adjacent a next sequential treatment pattern.

12. The method of claim 10, further including:

providing a template having an opening defining an outside dimension of the treatment region; and the step of scanning includes turning on the output beam while the propagation axis directs the output beam outside of the opening of the template;

scanning the propagation axis at a constant velocity across the opening while the output beam is on until the output beam is directed outside of the opening; and while the output beam is directed outside of the opening, repositioning the propagation axis of the output beam for a successive treatment pattern.

13. The method of claim 10, further including:

turning on and off the output beam in cooperation with the step of scanning to define a beginning and ending of the treatment pattern.

14. The method of claim 13, wherein said step of turning on and off the output beam is performed in cooperation with the step of scanning so that the output beam is turned on or off only while the propagation axis is being scanned at the control scan velocity.

15. The method of claim 9, wherein the treatment pattern consists essentially of a straight line having a width and a length.

16. The method of claim 9, wherein the treatment pattern consists essentially of a ring, having a radius and a radial width.

17. The method of claim 9, further including:

controlling intensity of the output beam and velocity of scanning cooperatively to control a fluence level in the treatment region for photocoagulation in tissue of the body.

18. A method for distributing a laser beam from a laser system for treatment of dermatology related disorders on skin, comprising:

placing portable beam aiming equipment adjacent a treatment area on the skin;

supplying the output beam to the beam aiming equipment;

directing the beam aiming equipment to define a propagation axis to the treatment area;

scanning the propagation axis of the laser beam at a controlled scan velocity, so that the laser beam essentially continuously scans a treatment pattern in a predetermined position within the treatment area on the skin;

successively repeating the step of scanning so that the laser beam scans a plurality of essentially continuously scanned treatment patterns in respective predetermined positions to fill the treatment area; and wherein the positions of successively scanned treatment patterns are controlled so that the position of a first sequential treatment pattern is non-adjacent the position of a next sequential treatment pattern.

19. The method of claim 18, wherein the treatment pattern consists essentially of a straight line having a width and a length.

20. The method of claim 18, wherein the treatment pattern consists essentially of a ring, having a radius and a radial width.

21. The method of claim 18, further including:

controlling intensity of the laser beam and velocity of scanning cooperatively to control a fluence level in the treatment area for photocoagulation of tissue in the treatment area.

22. The method of claim 18, further including:

providing a template having an opening defining an outside dimension of the treatment region; and the step of scanning includes turning on the laser beam while the propagation axis directs the laser beam outside of the opening of the template;

scanning the propagation axis at a constant velocity across the opening while the laser beam is on until the laser beam is directed outside of the opening; and while the laser beam is directed outside of the opening, repositioning the propagation axis of the laser beam for a successive treatment pattern.

23. The method of claim 18, further including:

turning on and off the laser beam in cooperation with the step of scanning to define a beginning and ending of the treatment pattern.

24. The method of claim 23, wherein said step of turning on and off the laser beam is performed in cooperation with the step of scanning so that the beam is turned on or off only while the propagation axis is being scanned at the control scan velocity.

25. A laser system for treatment of dermatology related disorders, comprising;

a laser supplying an output beam;

a transmissive fiber coupled to the laser and receiving the output beam of the laser;

a portable treatment head connected to receive the output beam through the transmissive fiber, and having a housing with a light transmissive opening adapted for placement adjacent a treatment area on skin;

means, mounted with the housing of the treatment head, for directing the output beam through the transmissive opening to a treatment area;

means, mounted with the housing of the treatment head and coupled with the means for directing, for scanning the output beam in a controlled velocity and direction to define an essentially continuous treatment pattern in the treatment area on the body; and means, coupled to the laser and the treatment head, for controlling the intensity of the output beam and controlling the means for scanning to establish an essentially constant fluence of radiation in the treatment area.

26. The laser system of claim 25, wherein the means for controlling establishes a fluence level in the treatment area sufficient for photocoagulation in the skin without burning or scarring of the skin.

27. The apparatus of claim 25, further including a template mounted with the housing of the treatment head to define a perimeter of the transmissive area; and wherein the control means is operative to generate a plurality of essentially non-overlapping treatment patterns to establish the constant fluence within the perimeter of the template.

28. The apparatus of claim 25, further including a structural spacer member, mounted with the housing of the treatment head, for establishing a preset distance from a body contacting the treatment head and the distal end of the transmissive fiber.

29. The apparatus of claim 28, further including a template mounted on the spacer member to define a perimeter of the transmissive opening; and wherein the control means is operative to generate a plurality of essentially non-overlapping treatment patterns to establish the constant fluence within the perimeter of the template.

30. The laser system of claim 25, wherein the treatment pattern consists essentially of a straight line having a width and a length greater than the width.

31. The apparatus of claim 25, wherein the treatment pattern consists essentially of a ring, having a radius and a radial width.

32. The apparatus of claim 25, wherein:

the means for directing comprises means for securing the transmissive fiber near the distal end, so that the output beam propagates along a propagation axis essentially transverse to, and having a position in, a scanning plane; and the means for scanning comprises means, coupled to the means for securing, for controlling the position of the propagation axis in the scanning plane.

33. The apparatus of claim 25, wherein:

the means for scanning comprises means, receiving the output beam from the fiber, for controlling direction of the beam in the treatment area.

* * * * *